US00PP11298P

United States Patent [19]

Boeder

[11] Patent Number: Plant 11,298

[45] Date of Patent: Mar. 21, 2000

[54] CHRYSANTHEMUM PLANT NAMED 'ROADRUNNER'

[75] Inventor: Mark Boeder, West Wittering, United Kingdom

[73] Assignee: Cleangro Limited, West Sussex, United Kingdom

[21] Appl. No.: 09/038,892

[22] Filed: Mar. 11, 1998

[51] Int. Cl.[7] ..... A01H 5/00

[52] U.S. Cl. ..... Plt./286

[58] Field of Search ..... Plt./286, 287, 289, Plt./295

[56] References Cited

U.S. PATENT DOCUMENTS

P.P. 8,803 6/1994 Fuess ..... Plt./287

OTHER PUBLICATIONS

UPOU–ROM, 1998/04, Plant Variety Database, GTI Jouve Retrieval Software, citation for GB BIL 01505315.

*Primary Examiner*—Howard J. Locker
*Attorney, Agent, or Firm*—Christie, Parker & Hale, LLP

[57] ABSTRACT

A new plant variety of Chrysanthemum producing yellow and red bicolor flowers.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Roadrunner'.

The female parent of the new variety is the variety known as 'Serenade Empire' (U.S. Plant Pat. No. 8,803) and the male parent is an undistributed, unnamed seedling identified as 'G12-C1'. The new variety has been asexually reproduced by vegetative cuttings in Ventura County, Calif. and the distinguishing characteristics are retained through successive generations of asexual reproduction.

SUMMARY OF THE INVENTION

'Roadrunner' is a pot type chrysanthemum plant variety that produces yellow and red bicolor flowers.

Comparison With 'Empire Serenade'

'Roadrunner' differs from 'Empire Serenade' in flower color. The new variety produces yellow and red bicolor flowers and 'Serenade'produces pink to red-purple flowers.

BRIEF DESCRIPTION OF ILLUSTRATIONS

The accompanying photographs show a typical specimen of potted plant of the new variety and of flowers of the new variety, with colors being as nearly true as possible with illustrations of this type. Terminal peduncle about 3 to 4 cm, lower most peduncle about 6 cm.

DESCRIPTION OF THE PLANT

Figure 1:
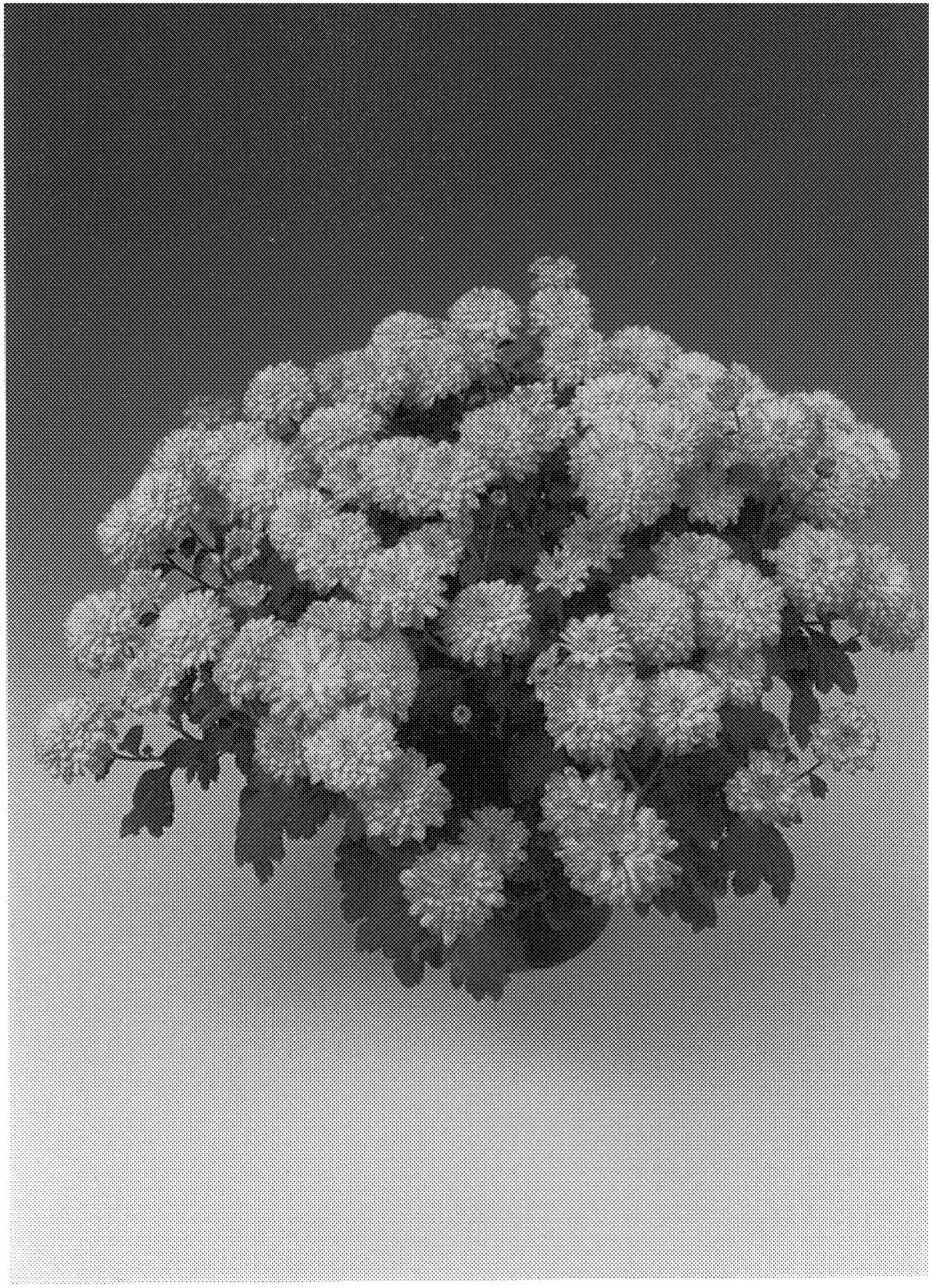
FIG. 1 is a whole plant view (from above) of the new cultivar grown in a pot.
Figure 2:
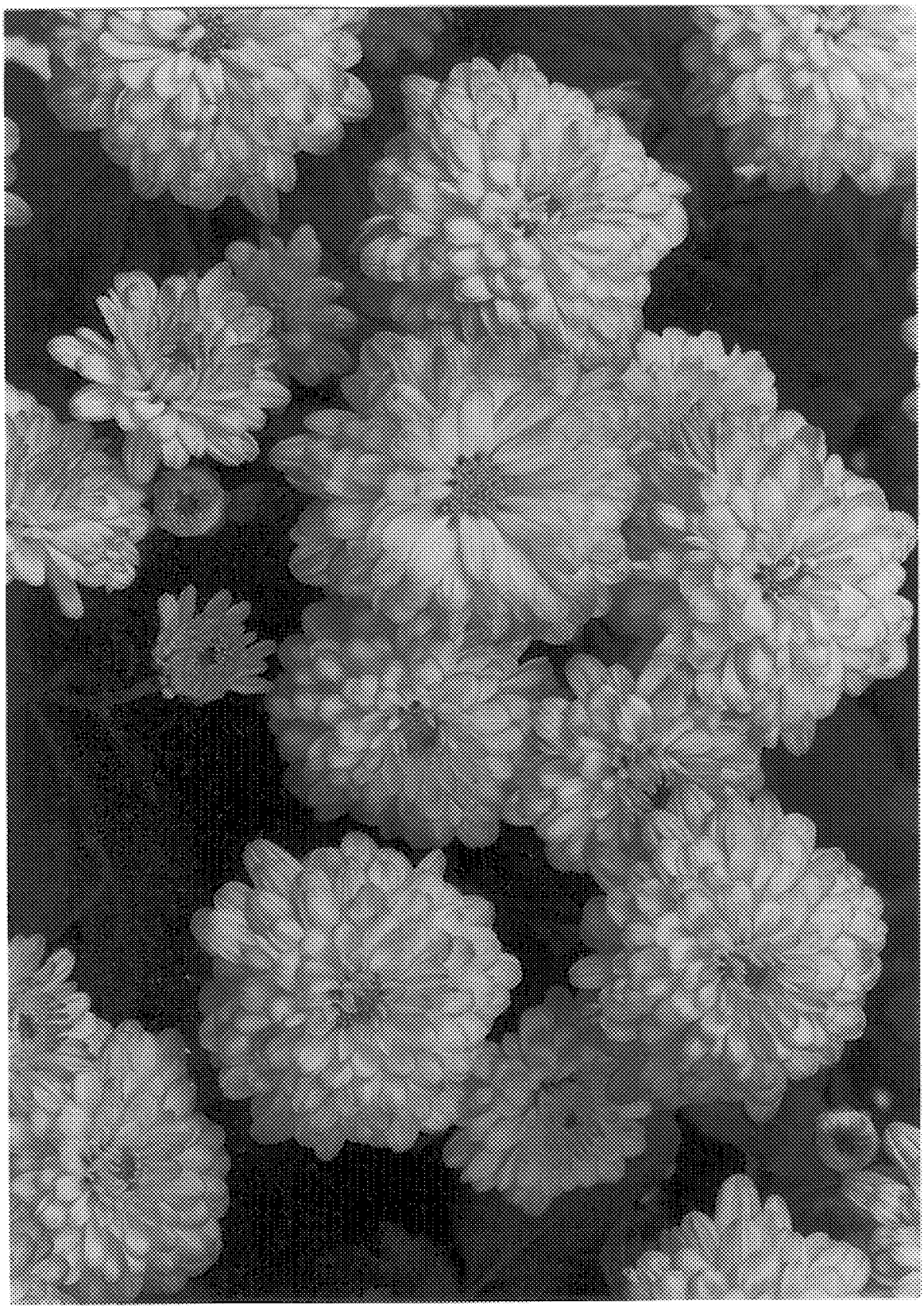
FIG. 2 shows inflorescence and foliage characteristics of the new cultivar in greater detail.

The following description of the new variety is of specimens grown in a greenhouse in Ventura County, Calif. in the month of October. 'Roadrunner' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 4 breaks per pinch. It has been observed that the shelf life of 'Roadrunner' is about 22 days with the response time of about 6.5 weeks. No treatment with growth retardant is required. Useful growing conditions include night temperatures of about 62°–66° F., day temperatures of about 80°–85° F. and about 5,000 foot-candles of light.

Plant:

*Habit.*—Mounding.
*Height.*—About 24 cm.
*Number of breaks from pinch.*—About 4.
*Typical container sizes commercially grown in.*—4 inch, 6 inch, 1 gallon, 3 gallon containers.
*Length of lateral branches.*—About 20 cm.
*Stem color.*—Near 146D.

Foliage:

*Leaf arrangement.*—Alternate.
*Number of leaves per lateral branch.*—About 13.
*Leaf size.*—Length: About 6.8 cm. Width: About 4 cm.
*Leaf shape.*—Ovate.
*Attachment.*—Petioled.
*Leaf apex.*—Obtuse.
*Base.*—Tapered.
*Margin.*—Lobed, crenate.
*Aspect.*—Slightly rolled under.
*Surface.*—Top: Pubescent. Bottom: Pubescent.
*Petiole length.*—About 1.5 cm. Color: Near 146D.
*Color.*—Mature leaf: Top Near 137A. Bottom: Near 137C. Young leaf: Top: Near 137A. Bottom: Near 138A.

Flower:

*Inflorescence form.*—Cyme.
*Flower form.*—Deplex daisy.
*Number of blooms per branch.*—About 6.
*Diameter of fully expanded bloom.*—About 5 cm.
*Depth of fully expanded bloom.*—About 3 cm.
*Sepal number.*—About 30. Color: Near 137A.
*Peduncle.*—Terminal peduncle about 3 to 4 cm, lower most peduncle about 6 cm. Habit: Straight. Surface: Pubescent. Strength: Weak.
*Flower bud shape.*—Flattened sphere. Diameter: About 0.8 cm. Height: About 0.5 cm.
*Ray florets.*—Number per flower: About 145. Shape: Oblanceolate. Apex: Obtuse. Base: Tapered. Margin:

Entire. Aspect: Reflexed back. Length: About 2.3 cm. Width: About 0.7 cm.

*Disc florets.*—Number per flower: About 40. Shape: Cylindrical. Length: About 0.5 cm. Width: About 0.08 cm.

*Fragrance.*—Faint.

Flower color:

*General flower coloration.*—Yellow with strong red streaks.

*Ray florets, top side.*—Immature: Near 9A with near 46A streaks. Mature: Near 9B with strong near 46A streaks. Fading: Near 9A, with very few near 46A streaks, more prominent at distal end.

*Ray floret, under side.*—Immature: Near 10B. Mature: Near 11B. Fading: Near 11C.

*Disc florets.*—Mature: Near 13A.

*Changes as the flower ages.*—Red streaking becomes more prominent at distal end.

Reproductive organs:

*Ray florets.*—Pistillate. Stigma shape: 2 branched. Stigma color: Near 7A. Style length: About 0.4 Cm.

*Disc florets.*—Stigma Shape: 2 branched. Stigma color: Near 9A. Style Length: About 0.4 cm. Stamen numbera: About 5. Anther length: About 0.4 cm. Pollen color: Near 15A. Pollen quantity: Aboundant.

What is claimed is:

1. A new and distinct Chrysanthemum plant of the variety substantially as herein shown and described.

* * * * *